(12) United States Patent
Zhu

(10) Patent No.: US 9,377,431 B2
(45) Date of Patent: Jun. 28, 2016

(54) HETEROJUNCTION NANOPORE FOR SEQUENCING

(71) Applicant: GLOBALFOUNDRIES INC., Grand Cayman (KY)

(72) Inventor: Wenjuan Zhu, Fishkill, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 384 days.

(21) Appl. No.: 13/949,824

(22) Filed: Jul. 24, 2013

(65) Prior Publication Data

US 2015/0028845 A1    Jan. 29, 2015

(51) Int. Cl.
*G01N 27/327*   (2006.01)
*G01N 33/487*   (2006.01)
*B82Y 15/00*    (2011.01)
*B82Y 30/00*    (2011.01)

(52) U.S. Cl.
CPC ............ *G01N 27/3275* (2013.01); *B82Y 15/00* (2013.01); *G01N 33/48721* (2013.01); *B82Y 30/00* (2013.01); *Y10S 977/773* (2013.01)

(58) Field of Classification Search
CPC .................... G01N 27/3275; G01N 33/48271; B82Y 15/00
USPC ......................................................... 422/500
See application file for complete search history.

(56) References Cited

U.S. PATENT DOCUMENTS 7,001,792 B2   2/2006   Sauer et al.
7,846,738 B2   12/2010  Golovchenko et al.
2007/0190542 A1   8/2007   Ling et al.
2008/0157354 A1   7/2008   Zhang et al.
2008/0185295 A1   8/2008   Briman et al.
2010/0066348 A1   3/2010   Merz et al.
2010/0327847 A1 * 12/2010   Leiber .................... B82Y 15/00
                                                    324/71.1

(Continued)

FOREIGN PATENT DOCUMENTS

CN    102169105 A    8/2011
EP    1037366 A2    9/2000

(Continued)

OTHER PUBLICATIONS

Liu, S. (2013). "Boron Nitride Nanopores: Highly sensitive DNA Single-Molecule Detectors." Advanced Materials. 25:4549-4554.*

(Continued)

*Primary Examiner* — Jill Warden
*Assistant Examiner* — Jacqueline Brazin
(74) *Attorney, Agent, or Firm* — Thompson Hine LLP

(57) ABSTRACT

A technique is provided for performing sequencing with a nanodevice. Alternating graphene layers and dielectric layers are provided one on top of another to form a multilayer stack of heterojunctions. The dielectric layers include boron nitride, molybdenum disulfide, and/or hafnium disulfide layers. A nanopore is formed through the graphene layers and the dielectric layers. The graphene layers are individually addressed by applying individual voltages to each of the graphene layers on a one to one basis when a particular base of a molecule is in the nanopore. Each of the graphene layers is an electrode. Individual electrical currents are measured for each of the graphene layers as the particular base moves from a first graphene layer through a last graphene layer in the nanopore. The base is identified according to the individual electrical currents repeatedly measured for the base moving from the first through last graphene layer in the nanopore.

7 Claims, 15 Drawing Sheets

(56) References Cited

U.S. PATENT DOCUMENTS

| | | | |
|---|---|---|---|
| 2011/0217763 | A1 | 9/2011 | Rasooly et al. |
| 2011/0236984 | A1 | 9/2011 | Sun et al. |
| 2011/0279125 | A1 | 11/2011 | Bedell et al. |
| 2012/0037919 | A1* | 2/2012 | Xu .................. B82Y 15/00 257/76 |
| 2012/0146162 | A1 | 6/2012 | Cho et al. |
| 2014/0190833 | A1 | 7/2014 | Lieber et al. |
| 2015/0160159 | A1* | 6/2015 | Afzali-Ardakani .... B82Y 15/00 204/602 |

FOREIGN PATENT DOCUMENTS

| | | | |
|---|---|---|---|
| EP | 2424092 | A1 | 2/2012 |
| WO | WO0181896 | A1 | 11/2001 |
| WO | WO2009020682 | A2 | 2/2009 |
| WO | WO2011082419 | A2 | 7/2011 |
| WO | 2012138357 | A1 | 10/2012 |
| WO | WO 2013016486 | * | 1/2013 |
| WO | WO2013016486 | A1 | 1/2013 |

OTHER PUBLICATIONS

A. K. Geim and K. S. Novoselov, "The Rise of Graphene," Nature Materials 6 183 (2007).

Gracheva M. E., Xiong A., Aksimentiev A., Schulten K., Timp G. And Leburton J. P., "Simulation of the Electric Response of DNA Translocation Through a Semiconductor Nanopore-Capacitor," Nanotechnology 17 622-633 (2006).

H. Im et al., "A Dielectric-Modulated Field-Effect Transistor for Biosensing," Published online: Jun. 24, 2007, Nature Nanotechnology, vol. 2, Jul. 2007, pp. 430-434.

J. Hass, W.A.de Heer and E.H. Conrad, "The Growth and Morphology of Epitaxial Multilayer Graphene," Journal of Physics: Condensed Matter. 20, 323202 (2008).

Heng J. B., Ho C., Kim T., Timp R., Aksimentiev A., Grinkova Y. V., Sligar S., Schulten K. and Timp G., "Sizing DNA Using a Nanometer-Diameter Pore," Biophys. J. 87 2905-91 (2004).

Kasianowicz J. J., Brandin E., Branton D. and Deamer D. W., "Characterization of Individual Polynucleotide Molecules Using a Membrane Channel," Proc. Natl Acad. Sci. USA 93 13770-773 (1996).

K. S. Kim, et al., "Large-Scale Pattern Growth of Graphene Films for Stretchable Transparent Electrodes," Nature 457, 706-710 (2009).

Lagerqvist J., Zwolak M. and Di Ventra M., "Fast DNA Sequencing via Transverse Electronic Transport," Nano Lett. 6 779-782 (2006).

Meller A., Nivon L., Brandin E., Golovchenko J. and Branton D., "Rapid Nanopore Discrimination Between Single Polynucleotide Molecules," Proc. Natl Acad. Sci. USA 97 1079-84 (2000).

D. Farmer, et al., "Vertical Stacking of Graphene in a Field-Effect Transistor," U.S. Appl. No. 13/683,148, filed Nov. 21, 2012.

H. Peng, et al., "Graphene Transistor Gated by Charges Through a Nanopore ofr Bio-Molecule Sensing and DNA Sequencing," U.S. Appl. No. 13/448,509, filed Apr. 17, 2012.

Fernando Patolsky, Gengfeng Zheng, Oliver Hayden, Melike Lakadamyali, Xiaowei Zhuang, and Charles M. Lieber, "Electrical detection of single viruses," Departments of Chemistry and Chemical Biology and Physics and Division of Engineering and Applied Sciences, Harvard University, Cambridge, MA 02138, Contributed by Charles M. Lieber, Aug. 20, 2004, pp. 1-6.

H. W. C. Postma, "Rapid Sequencing of Individual DNA Molecules in Graphene Nanogaps," Nano Lett., vol. 10, No. 2, Publication Date (Web): Jan. 4, 2010, pp. 420-425.

J. Prasongkit et al., "Transverse Conductance fo DNA Nucleotides in a Graphene Nanogap from First Principles," arXiv:1012.1669v2 [physics.ins-det], [v1] Dec. 8, 2010, [v2] Jan. 14, 2011, Nano Lett., vol. 11, No. 5, 2011, pp. 1941-1945.

Soni G., and Meller A., "Progress Towards Ultrafast DNA Sequencing Using Solid State Nanopores," Clin. Chem. 3 1996-01 (2007).

Eric Stern, James F. Klemic, David A. Routenberg, Pauline N. Wyrembak, Daniel B. Turner-Evans, Andrew D. Hamilton, David A. Lavan, Tarek M. Fahmy and Mark A. Reed, "Label-free immunodetection with CMOS-compatible semiconducting nanowires," Nature Publishing Group, vol. 445, Feb. 2007, doi:10.1038/nature05498, pp. 1-4.

Storm A. J., Chen J. H., Ling X. S., Zandbergen H. W., and Dekker C., "Fabrication of Solid-State Nanopores with Single-Nanometre Precision," Nature Materials 2, 537-540 (2003).

S. Vassanelli, P. Fromherz, "Transistor Probes Local Potassium Conductances in the Adhesion Region of Cultured Rat Hippocampal Neurons," The Journal of Neuroscience, Aug. 15, 1999, 19(16):6767-6773, Department of Membrane and Neurophysics, Max-Planck-Institute for Biochemistry.

R. Akeson M., Branton D., Kasianowicz J. J., Brandin E., and Deamer D. W., "Microsecond Timescale Discrimination Among Polycytidylic Acid, Polyadenylic Acid, and Polyuridylic Acid as Homopolymers or as Segments within Single RNA Molecules," Biophys. J. 77 3227-33 (1999).

Y. He, et al., "Bilayer Graphene Lateral Contacts for Dna Sequencing," arXiv preprint arXiv: 1206.4199, 2012, 16 pages.

C. Palego, et al., "Nanopore Test Circuit for Single-Strand DNA Sequencing," 12th Topical Meeting on Silicon Monolithic Integrated Circuits in RF Systems (SiRF), 2012, pp. 101-104.

B. Venkatesan, et al., "Stacked Graphene-Al2O3 Nanopore Sensors for Sensitive Detection of DNA and DNA-Protein Complexes," ACS Nano, vol. 6, No. 1, 2011, pp. 441-450.

Bae, S. et al., "Roll-to-Roll Production of 30-Inch Graphene Films for Transparent Electrodes," Nature Nanotechnology 5 574 (2010).

A. Bergvall et al., "Graphene Nanogap for Gate-Tunable Quantum-Coherent Single-Molecule Electronics," Phys. Rev. B., vol. 84, No. 15, 2011, 155451, 7 pages.

Branton D., et al., The Potential and Challenges of Nanopore Sequencing, Nature Biotechnology 26(10) 1146-1153 (2008).

Luan, B., et al., "Tribological Effects on DNA Translocation in a Nanochannel Coated with a Self-Assembled Monolayer," Journal of Physical Chemistry B 114 (2010): 17172-7176.

* cited by examiner

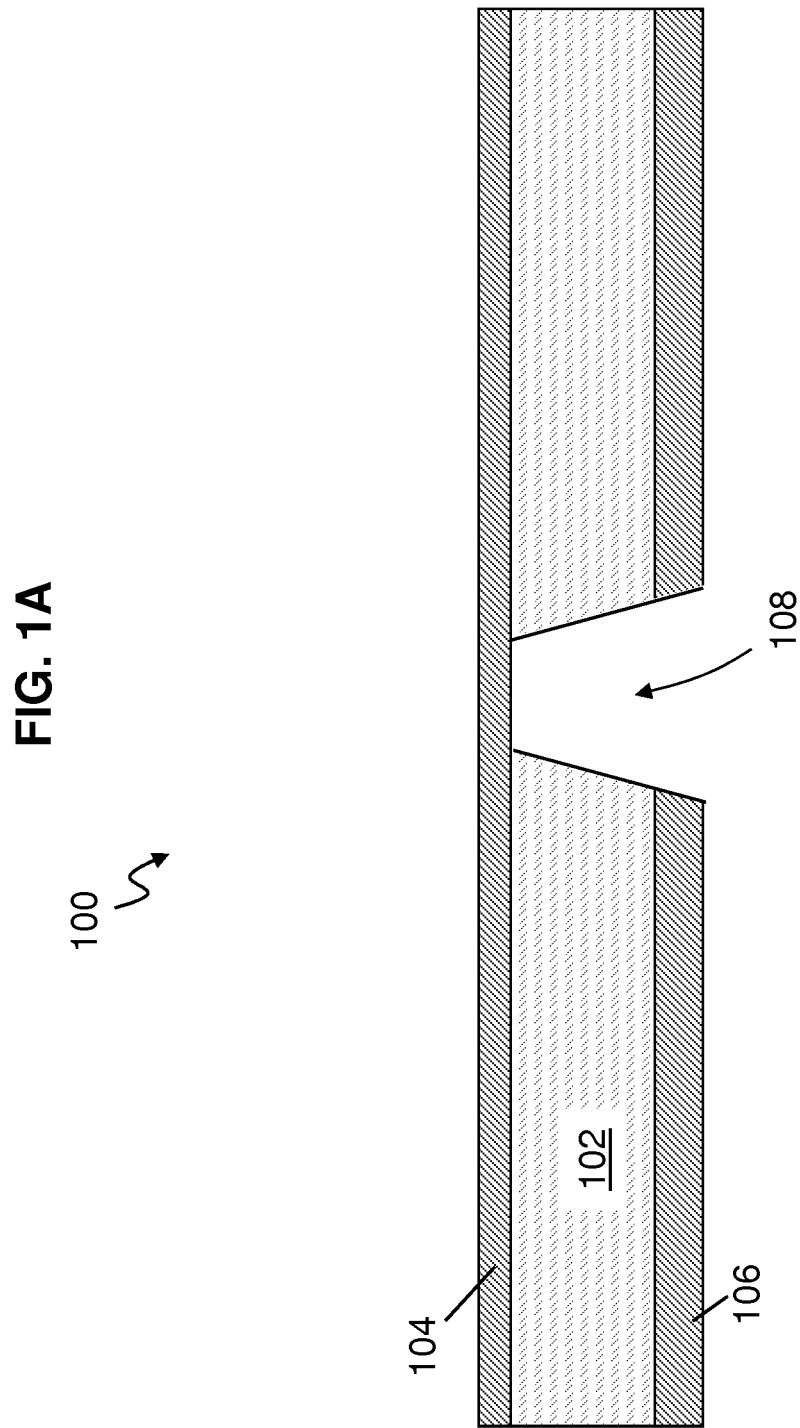

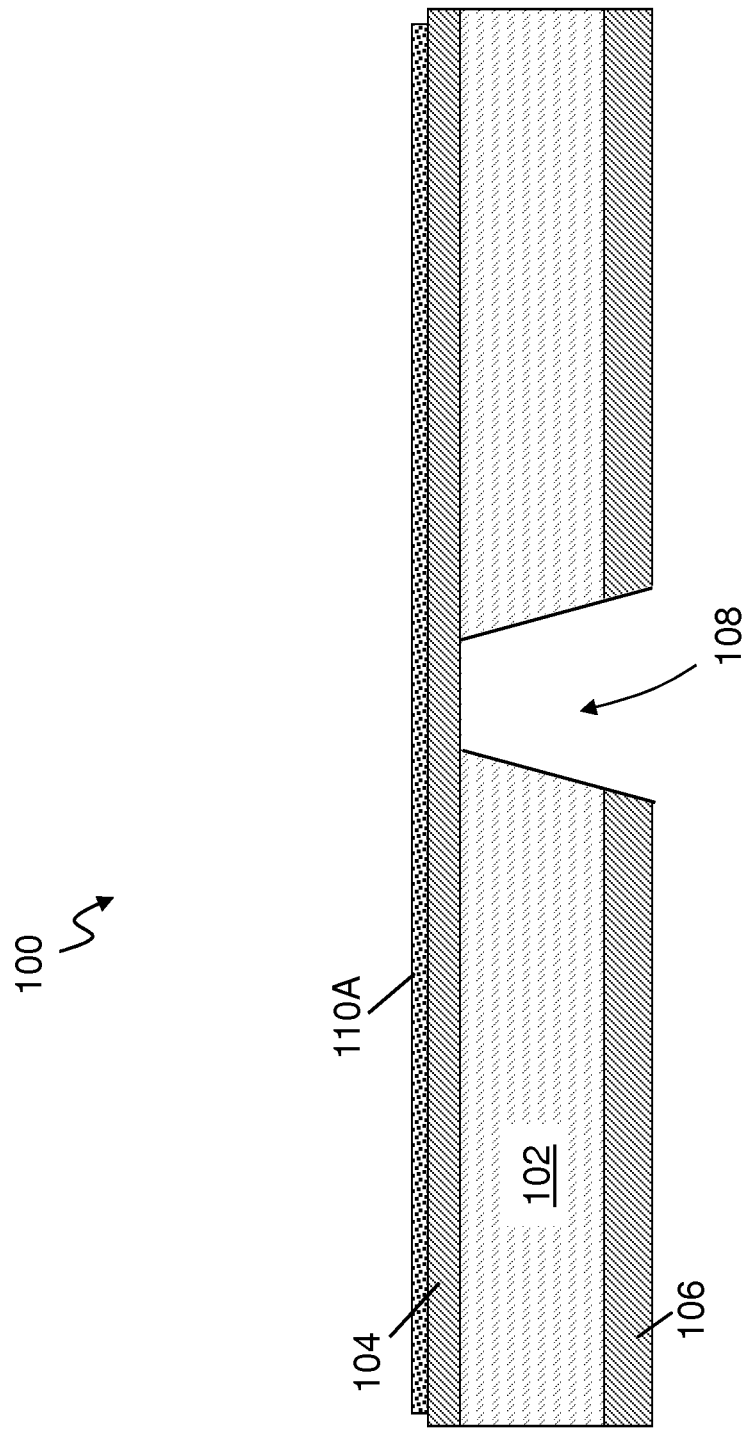

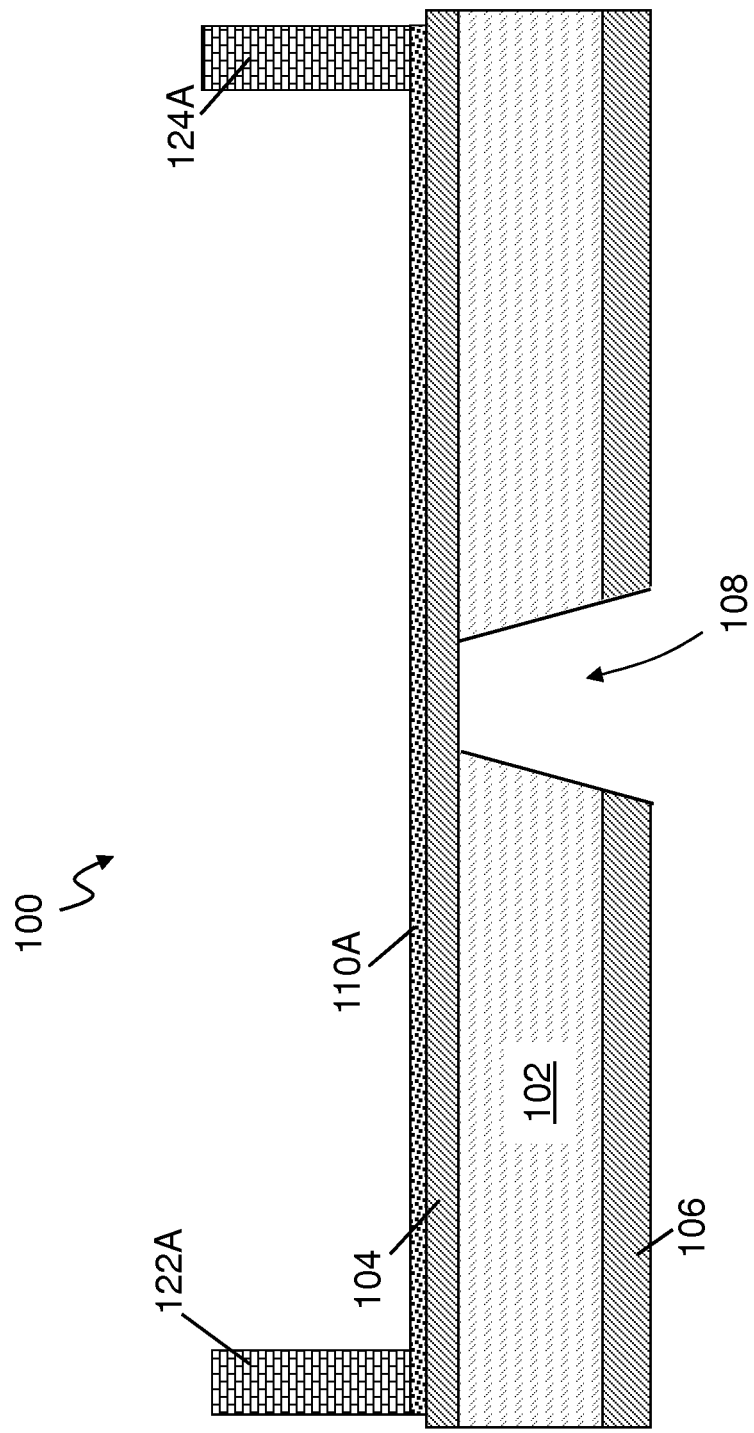

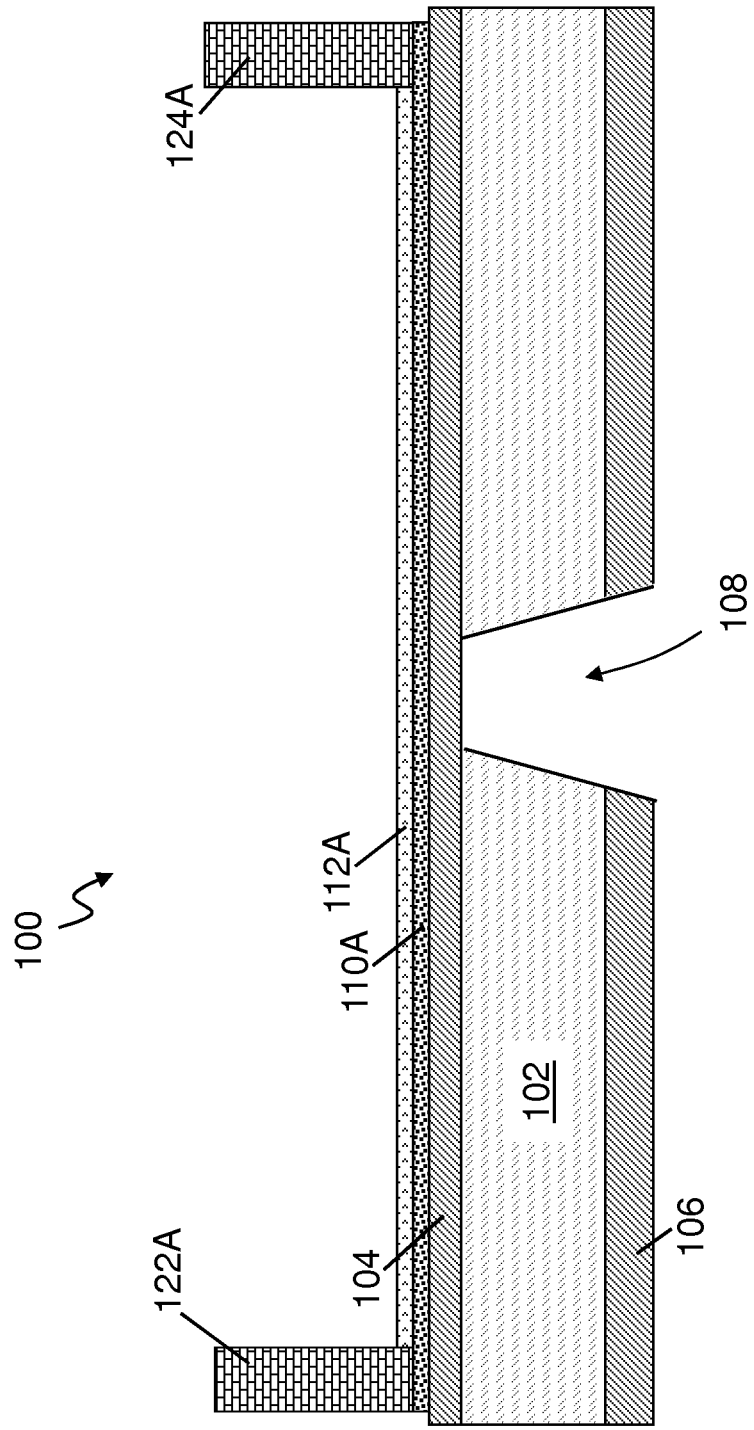

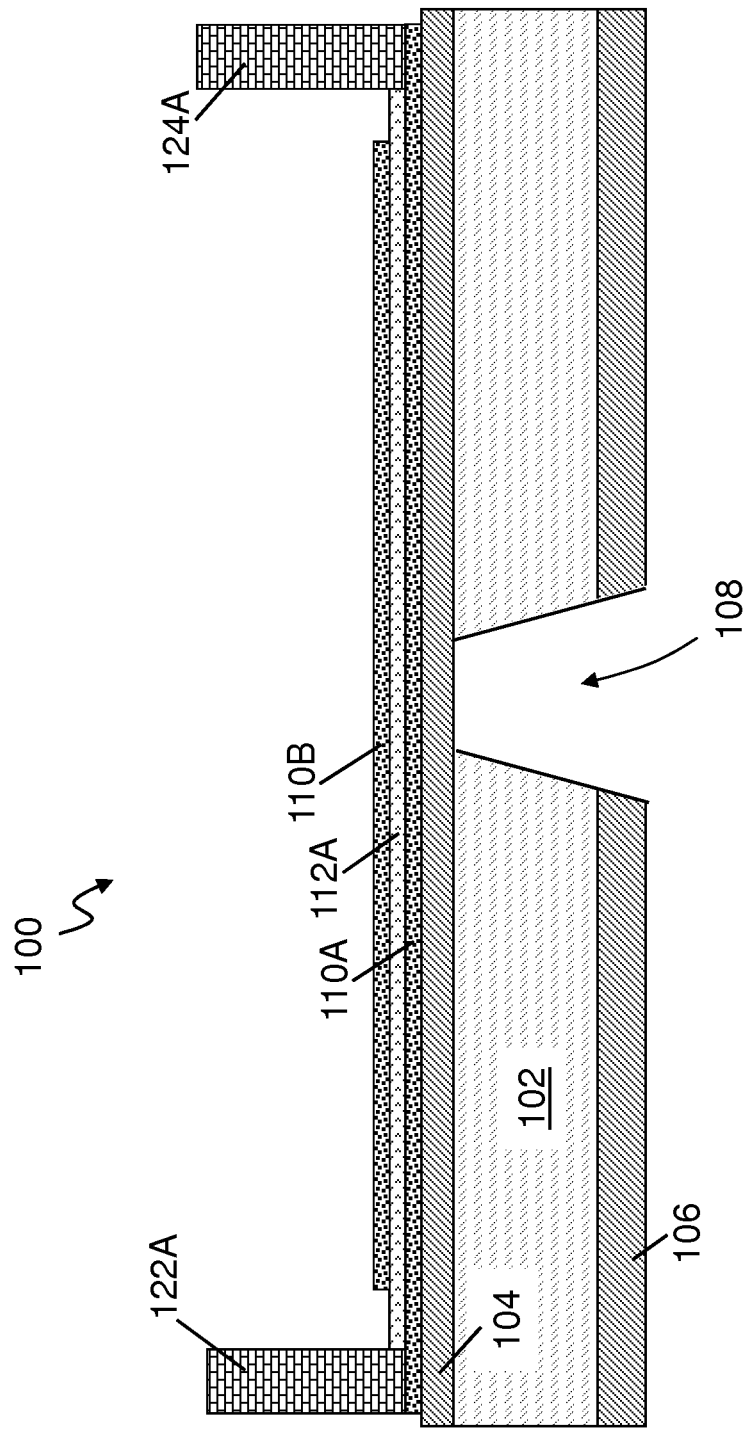

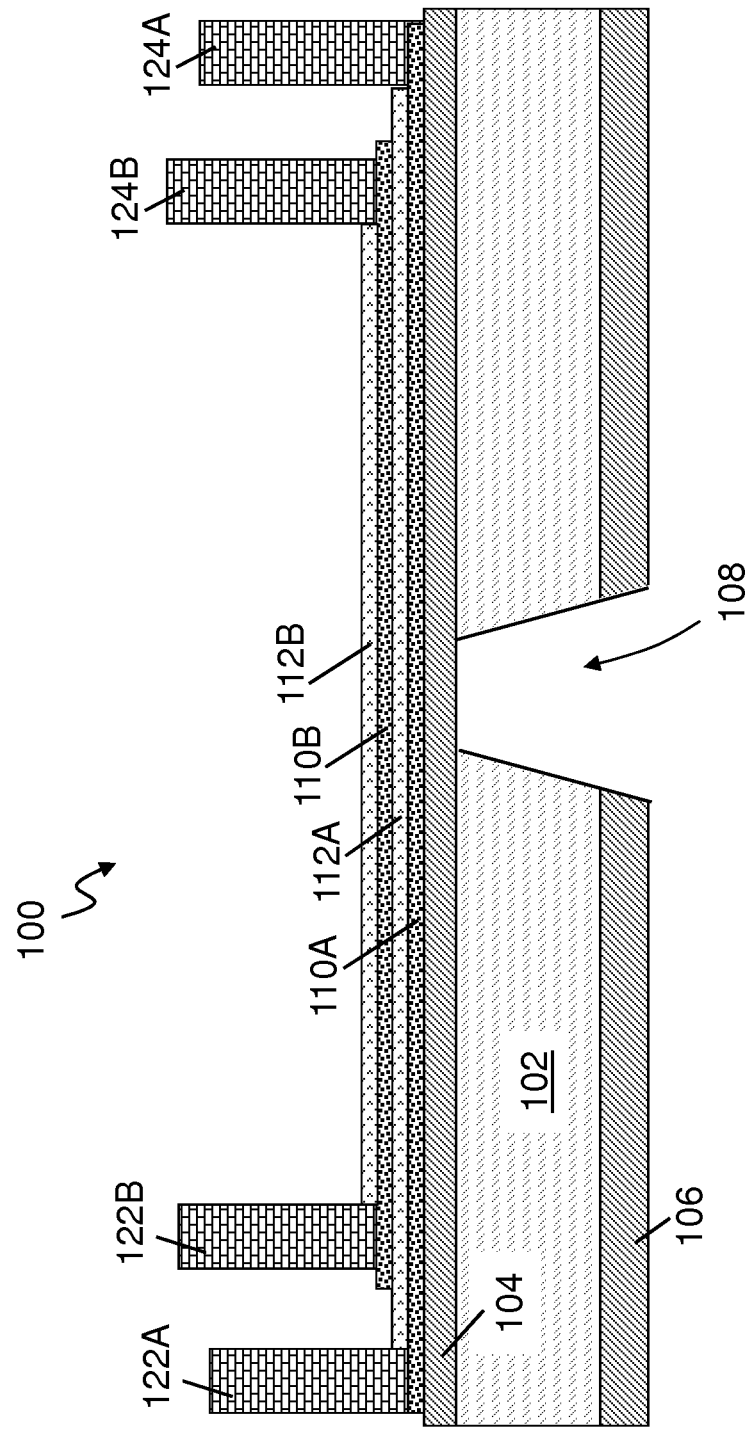

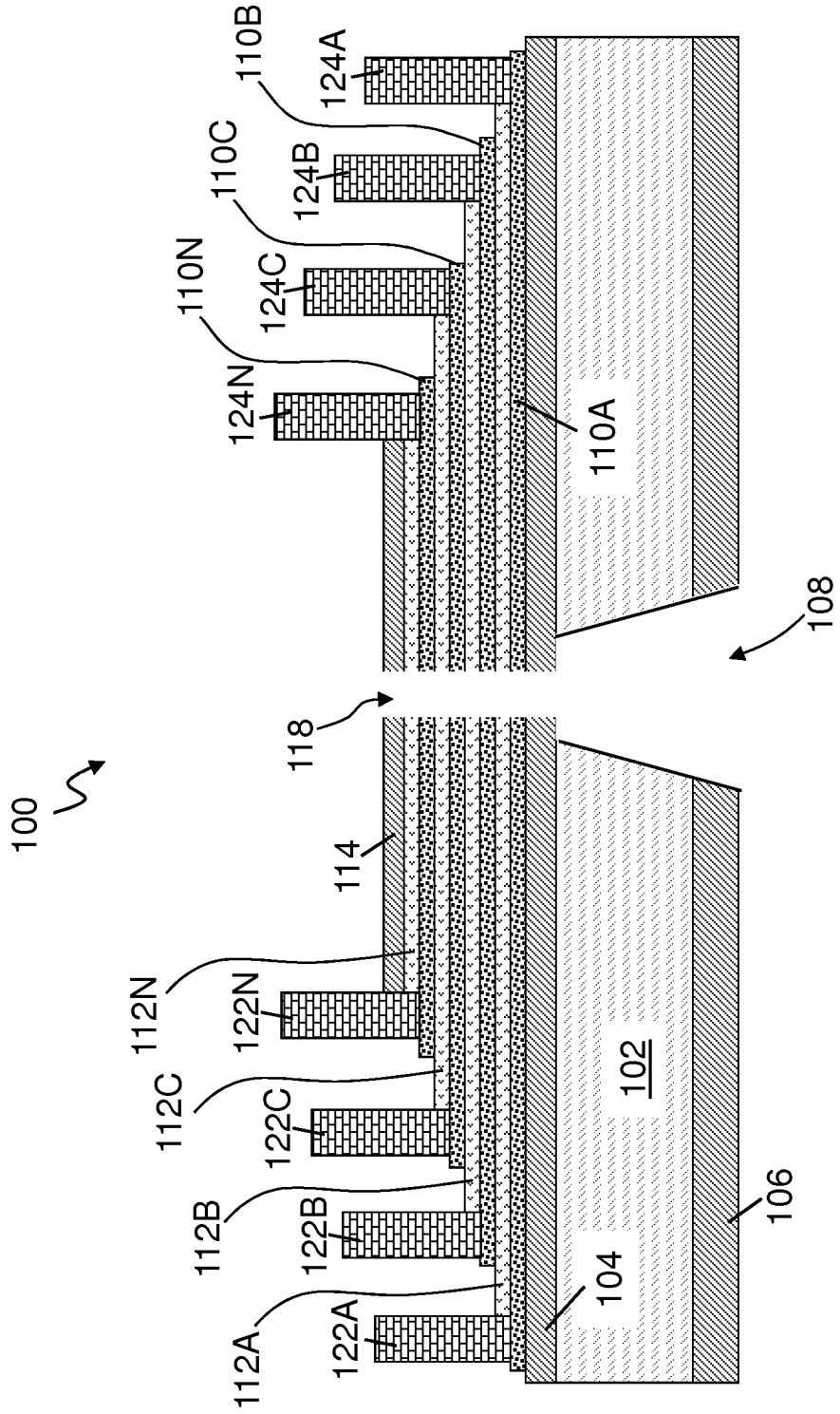

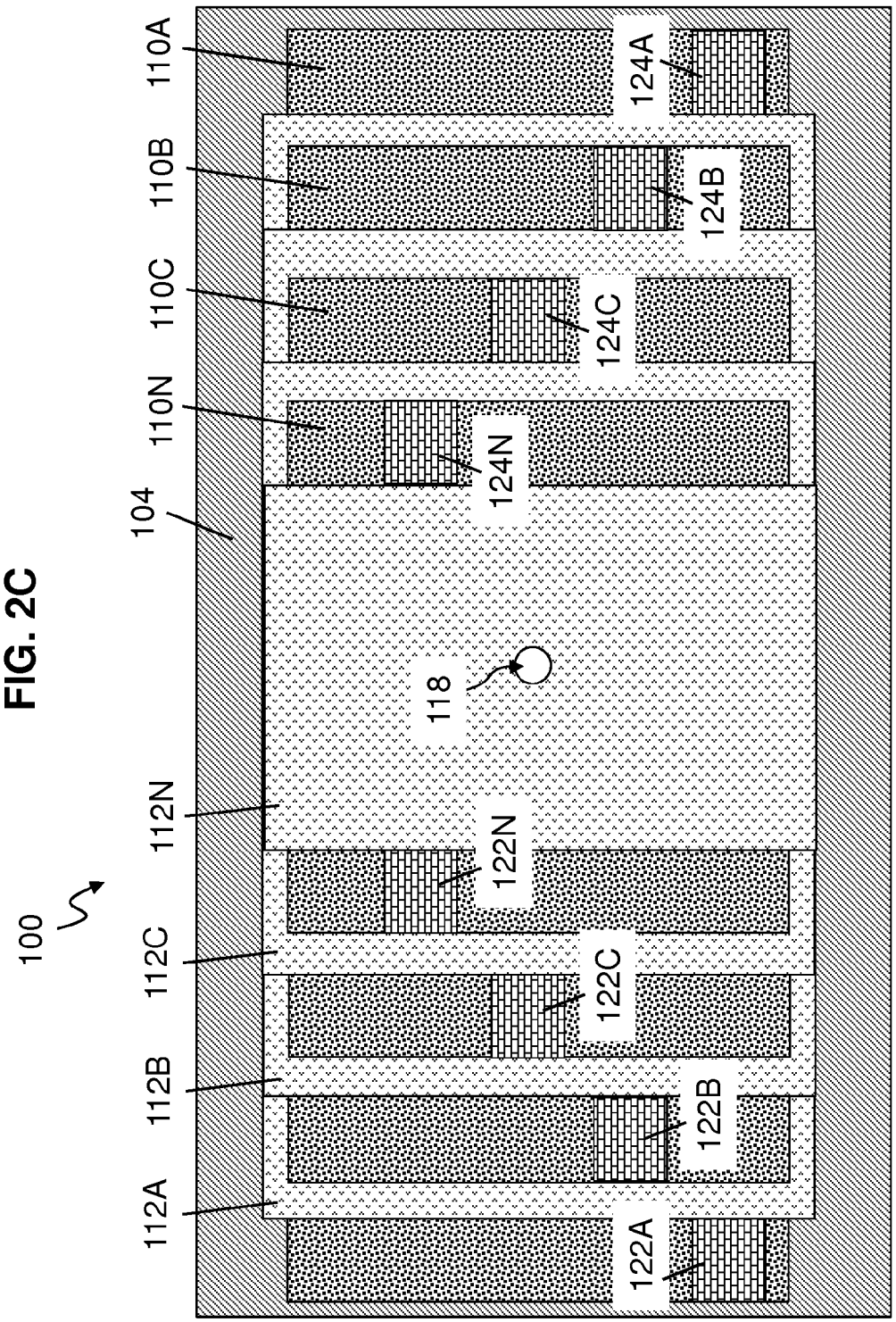

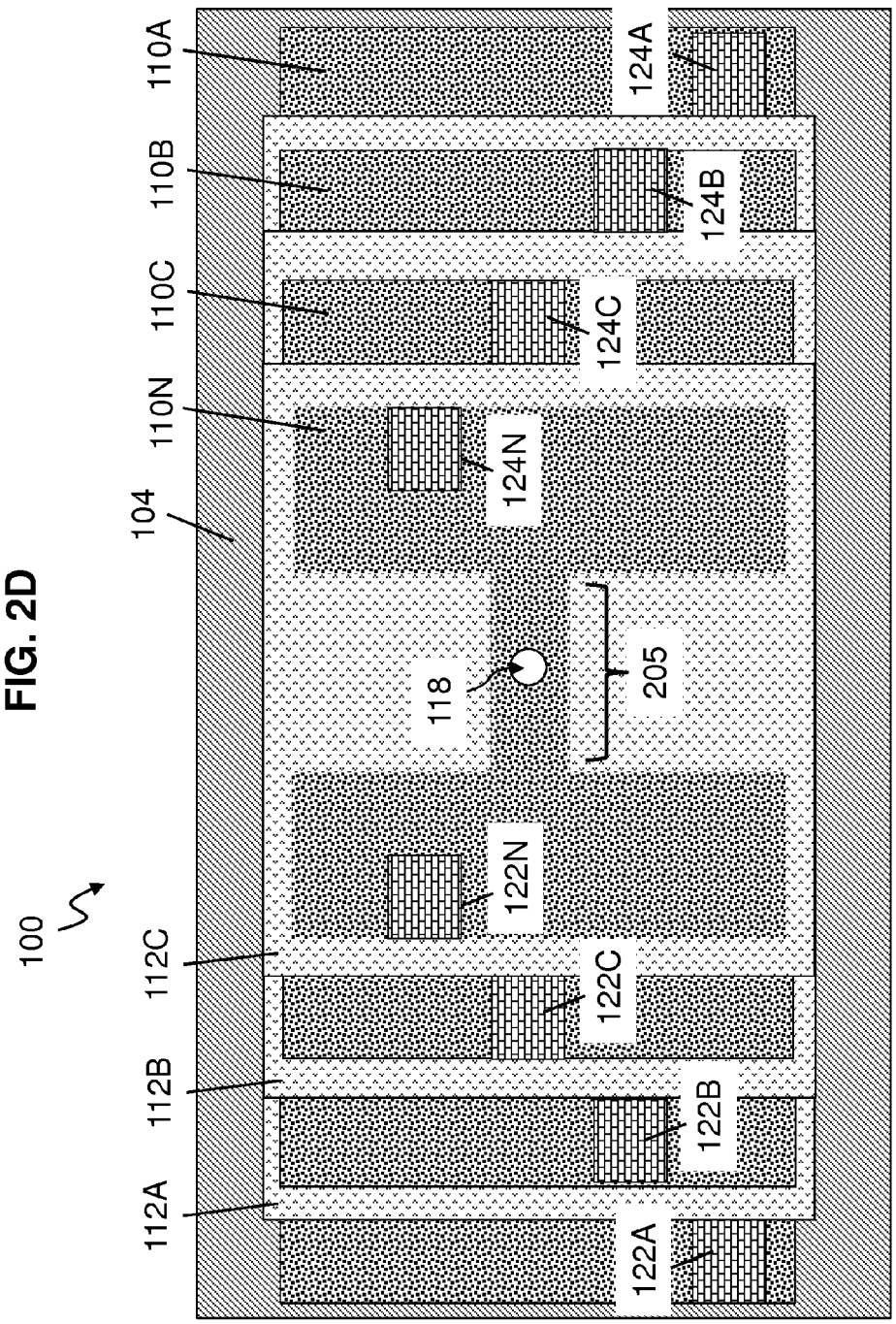

Respectively measure individual electrical currents for each of the graphene layers as the particular base moves from a first graphene layer through a last graphene layer in the nanopore 425

Determine an identification of the particular base according to the individual electrical currents repeatedly read for the particular base moving from the first graphene layer through the last graphene layer in the nanopore 430

HETEROJUNCTION NANOPORE FOR SEQUENCING

BACKGROUND

The present invention relates generally to nanodevices, and more specifically, to a multi junction or heterojunction nanopore for sequencing molecules.

Nanopore sequencing is a method for determining the order in which nucleotides occur on a strand of deoxyribonucleic acid (DNA). A nanopore (also referred to as pore, nanochannel, hole, etc.) can be a small hole in the order of several nanometers in internal diameter. The theory behind nanopore sequencing is about what occurs when the nanopore is submerged in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be positioned around the nanopore so that DNA bases can be differentiated while the DNA passes through the nanopore.

The DNA can be driven through the nanopore by using various methods, so that the DNA might eventually pass through the nanopore. The scale of the nanopore can have the effect that the DNA may be forced through the hole as a long string, one base at a time, like thread through the eye of a needle. Recently, there has been growing interest in applying nanopores as sensors for rapid analysis of biomolecules such as deoxyribonucleic acid (DNA), ribonucleic acid (RNA), protein, etc. Special emphasis has been given to applications of nanopores for DNA sequencing, as this technology holds the promise to reduce the cost of sequencing below $1000/human genome.

SUMMARY

According to one embodiment, a method of performing sequencing with a nanodevice is provided. The method includes providing alternating graphene layers and dielectric layers one on top of another to form a multilayer stack of heterojunctions, where the dielectric layers include boron nitride layers, molybdenum disulfide layers, and/or hafnium disulfide layers. The method includes forming a nanopore through each of the graphene layers and the dielectric layers, and individually addressing each of the graphene layers by applying individual voltages to each of the graphene layers on a one to one basis when a particular base of a molecule is in the nanopore. Each of the graphene layers is an electrode. The method includes respectively measuring individual electrical currents for each of the graphene layers as the particular base moves from a first graphene layer through a last graphene layer in the nanopore, and determining an identification of the particular base according to the individual electrical currents repeatedly measured for the particular base moving from the first graphene layer through the last graphene layer in the nanopore.

According to one embodiment, an apparatus for sequencing is provided. A nanodevice includes alternating graphene layers and dielectric layers one on top of another to form a multilayer stack of heterojunctions. The dielectric layers include boron nitride layers, molybdenum disulfide layers, and/o hafnium disulfide layers. The nanodevice includes a nanopore through each of the graphene layers and the dielectric layers, and electrodes individually addressed to each of the graphene layers. The electrodes apply individual voltages to each of the graphene layers on a one to one basis when a particular base of a molecule is in the nanopore.

According to one embodiment, a method of forming a nanodevice for sequencing is provided. The method includes disposing alternating graphene layers and dielectric layers one on top of another to form a multilayer stack of heterojunctions, where a first graphene layer of the graphene layers is initially disposed on an insulator that is disposed on a substrate. The dielectric layers include boron nitride layers, molybdenum disulfide layers, and/or hafnium disulfide layers. The method includes drilling a nanopore through each of the graphene layers and the dielectric layers, and disposing pairs of metal electrodes onto the graphene layers at opposing ends, such that each of the graphene layers is individually connected to only one pair of metal electrodes.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

FIGS. 1A through 1G illustrate cross-sectional views of a process of forming a heterojunction nanopore in a nanodevice for sequencing according to an embodiment, in which:

FIG. 1A illustrates a cross-sectional view of a substrate and insulator layers of the nanodevice;

FIG. 1B illustrates a cross-sectional view of depositing/transferring a (first) graphene layer on top of the insulator layer;

FIG. 1C illustrates a cross-sectional view of depositing metal electrodes;

FIG. 1D illustrates a cross-sectional view of depositing a first dielectric layer on top of the first graphene layer;

FIG. 1E illustrates a cross-sectional view of depositing a second graphene layer on top of the first dielectric layer;

FIG. 1F illustrates a cross-sectional view of depositing second metal electrodes on top of the second graphene layer and depositing a second dielectric layer on top of the second graphene layer; and FIG. 1G illustrates a cross-sectional view of the nanodevice after repeatedly performing operations in FIGS. 1B through 1F to deposit pairs of graphene layers and dielectric layers, along with corresponding metal electrodes.

FIG. 2C illustrates an example of a top view in which the metal electrodes are staggered according to an embodiment.

FIG. 2D illustrates the example of the top view in which the metal electrodes are staggered and an upper layer lifted off to show underneath according to an embodiment.

DETAILED DESCRIPTION

Figure 2A:
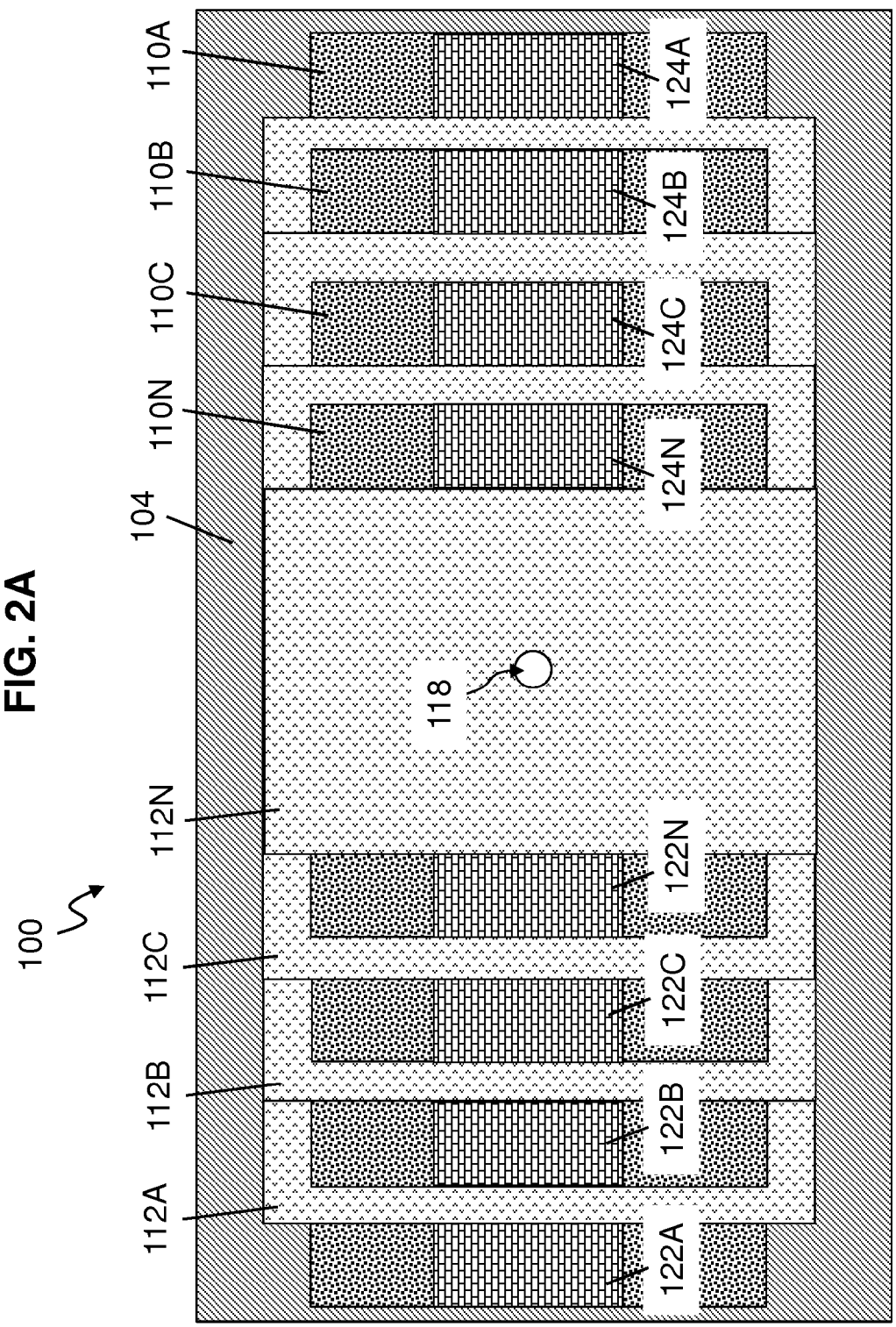
FIG. 2A illustrates a top view of the nanodevice according to an embodiment.

As noted above, DNA (or RNA) sequencing is the process of determining the precise order of nucleotides within a DNA molecule. Knowledge of DNA sequences is very useful for basic biological research, and in numerous applied fields such as diagnostic, biotechnology, forensic biology, and biological systematics. Recently, nanopore devices attract intense interest as a promising structure for DNA sequencing. A nanopore typically contains a thin film with a nano-sized pore in the film. The thin film typically contains one metal layer to detect an electrical signal and a few insulating layers for insulation and mechanical support. When DNA passes through the nanopore, an electrical signal can be detected. The electrical signal may be induced by the DNA blockage of the ionic current in the nanopore and/or induced by the electrical charge on the DNA base. However, since the position and movement of the DNA in the ionic solution are highly random, the error rate for this nanopore structure is typically very high.

Embodiments provide a (multi) heterojunction stack nanopore structure for DNA sequencing. In each junction, there is one layer of metal (and one layer of an insulator). In this structure, each DNA base passes multiple metal sensing layers (e.g., graphene) sequentially, such that the same DNA base is read multiple times as the DNA base passes through the nanopore. By analyzing (e.g., via a computer) the read out for each base statistically (i.e., the multiple reads of ionic (electrical) current measured for the same base at different intersections of the graphene layer), the error rate can be significantly reduced. More specifically, embodiments propose multiple graphene/boron nitride heterojunction stacks and/or multiple graphene/molybdenum disulfide ($MoS_2$) and/or hafnium disulfide layers heterojunction stacks to form the nanopore structure for DNA sequencing. Since graphene, boron nitride, and molybdenum disulfide can all be made atomically thin, the resolution of the nanodevice is much higher than typical metal/oxide or metal/nitride structure, and the heterojunction nanopore structure further improves the accuracy of the reading (for each base).

FIGS. 1A through 1G illustrate cross-sectional views of a process of forming a heterojunction nanopore for DNA sequencing according to an embodiment. The heterojunction nanopore is a nanodevice 100 that has multiple measuring points/junctions (each is the location between two electrodes) for repeatedly measuring the electrical current (i.e., the change of electrical current when voltage is applied to the two electrodes) of the same base of a molecule (e.g., a DNA or RNA molecule), as that base traverses through the nanopore.

FIG. 1A illustrates a cross-sectional view of the nanodevice 100. The nanodevice 100 has a substrate 102. The substrate 102 may be a silicon substrate (e.g., a wafer). Insulator 104 may be grown on and/or deposited on top of the substrate 102. Insulator 106 may be grown and/or deposited on the bottom of the substrate 102. To form a cavity 108, the insulator 106 and the substrate 102 are etched using lithography and a wet etch as understood by one skilled in the art. The thickness of insulator 104 may be in the range of 20 to 40 nanometers (nm). The thickness of insulator 106 may be in the range of 200 to 300 nanometers (nm). The insulators 104 and 106 may be any material that does not conduct electricity, such as silicon dioxide or silicon nitride.

FIG. 1B illustrates a cross-sectional view of depositing/transferring a (first) graphene layer 110A on top of the insulator layer 104. The multiple layers of graphene are deposited (such that each side of the graphene acts as an electrode as discussed further). The graphene layer 110A may be patterned using lithography and oxygen plasma. As the graphene layer 110A (along with subsequent graphene layers 110) can be as thin as 0.335 nm (nanometers), the spatial resolution of this approach can be 0.335 nm, which is sufficient spatial resolution for DNA sequencing purposes. The graphene was synthesized by a CVD method on copper (Cu) foil. After graphene formation, PMMA (polymethyl methacrylate) was spin-coated on top of the graphene layer formed on one side of Cu foil. This Cu foil was then dissolved in a copper etchant. The resulting graphene/PMMA layer was transferred to a $SiO_2$/Si substrate, where the PMMA was later dissolved in acetone.

FIG. 1C illustrates a cross-sectional view of depositing metal electrodes 122A and 124A. The metal electrodes 122A and 124A (including subsequent metal electrodes) are deposited on and/or beside the graphene layer 110A (or respective subsequent graphene layers), such that the metal electrodes 122A and 124A are in contact (i.e., physical and electrical) with the graphene layer 110A. The metal electrode 122A is on top of the left side of the graphene layer 110A and metal electrode 124A is on the right side. The material of the metal electrodes 122A and 124A (including subsequent metal electrodes) may be include gold, titanium, palladium, tungsten, aluminum, etc., or combination of these metals.

FIG. 1D illustrates a cross-sectional view of depositing a (first) dielectric layer 112A (e.g., an insulating layer) on top of the first graphene layer 110A. The dielectric layer 112A may abut the metal electrodes 122A and 124A. The dielectric layer 112A (and subsequent dielectric layers) may each be boron nitride, $MoS_2$, $HfS_2$, and/or another layered two-dimensional (2D) material with a large band gap.

FIG. 1E illustrates a cross-sectional view of depositing a second graphene layer 110B on top of the first dielectric layer 112A. The second graphene layer 110B is patterned such that it does not touch the metal electrodes 122A and 124A.

FIG. 1F illustrates a cross-sectional view of depositing a second metal electrode 122B and a second metal electrode 124B on top of the second graphene layer 110B. The second metal electrode 122B is on the left side of the graphene layer 110B while the second metal electrode 124B is on the right side. A second dielectric layer 112b is deposited on the second graphene layer 110B, and the dielectric layer 112B abuts the metal electrodes 122B and 124B.

The operations performed in FIGS. 1B through 1F are repeated to transfer/deposit other pairs of graphene layers and dielectric layers (as many as desired), along with depositing subsequent metal electrodes. FIG. 1G illustrates a cross-sectional view of nanodevice 100 with graphene layers 110A through 110N, where 110N represents the last graphene layer. The nanodevice 100 also shows dielectric layers 112A through 112N, wherein 112N is the last dielectric layer.

The first metal electrode 122A through the last metal electrode 122N are shown in FIG. 1G, where the last metal electrode 122N is the last one of the metal electrodes 122 on the left side. The first metal electrode 124A through the last metal electrode 124N are shown, where the last metal electrode 124N is the last one of the metal electrodes 124 on the right side.

Optionally, an insulator layer 114 is deposited on top of the last dielectric layer 112N to touch the metal electrodes 122N and 124N. The thickness of the insulator 114 is in the range of 10 to 40 nm. This thick insulator layer 114 provides additional protection and electrical isolation of the graphene layers 110 from the ionic buffer solution (solution 350 shown in FIG. 3).

Also, a nano-sized hole, nanopore 118, is drilled through the optional insulator 114, the graphene layers 110A through 110N, and the dielectric layers 112A through 112N. The nanopore 118 can be drilled using a transmission electron microscope (TEM) or reactive ion etch (RIE).

Figure 2B:
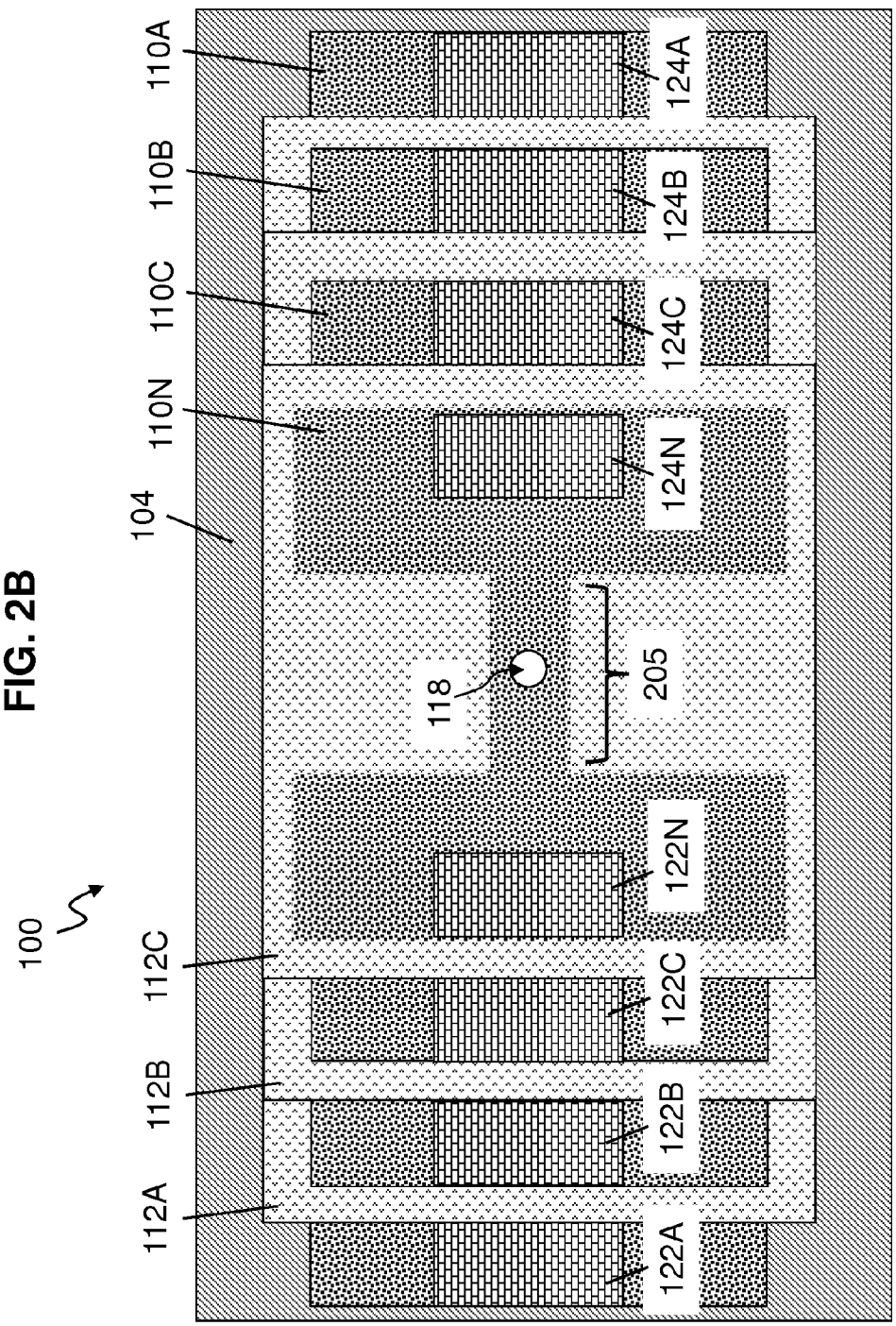
FIG. 2B illustrates the top view of the nanodevice with an upper layer lifted off to show underneath according to an embodiment.

FIG. 2A illustrates a top view of the nanodevice 100 according to an embodiment. In FIG. 2A, each of the metal electrodes 122A though 122N and each of the metal electrodes 124A through 124N are shown in a line (from left to right). FIG. 2B shows the top view of a narrowed graphene strip 205 (of the graphene layer 110N) underneath the dielectric layer 112N. Note the graphene layers 110A through 110N are each patterned to be narrower at the center (i.e., each has its own narrowed graphene strip 205) where the nanopore 118 is located in order to increase the sensitivity of the respective graphene layers 110A through 110N (when measuring electrical current with a DNA base present). The narrower the graphene strip 205, the larger percentage change of the conductivity along the graphene film (i.e., graphene layer 110) induced by the DNA base. The graphene at the contact region (with respective electrode pairs 122 and 124) is wider in order to reduce contact resistance. The graphene strip 205 width at the center is in the range of 1 to 200 nm. The nanopore 118 size (diameter) is in the range of 0.5 to 100 nm, which is to correspond to (i.e., fit within) the width of the graphene strip 205. For example, if the graphene strip 205 is 1 nm wide, the nanopore 118 has a diameter of 0.5. If the graphene strip 205 is 3 nm wide, the nanopore 118 may have a diameter of 1 nm (i.e., the diameter of the nanopore 118 is smaller than the width of the graphene strip 205).

Additionally, FIG. 2C illustrates an example of a top view in which the metal electrodes 122A through 122N and metal electrodes 124A through 124N are staggered according to an embodiment. In this case, the metal electrodes 122A through 122N and metal electrodes 124A through 124N are not all lined up in a row. Rather, there is a first pair of metal electrodes 122A and 124A in the front on the first graphene layer 110A, a second pair of metal electrodes 122B and 124B on the second graphene layer 110B behind the first pair, and so forth until the last pair of metal electrodes 122N and 124N. For the staggered metal electrodes 122A through 122N, FIG. 2D shows the top view of the narrowed graphene strip 205 (of the graphene layer 110N) underneath the dielectric layer 112N (as discussed above in FIG. 2B). The dielectric layer 112N has been lifted off so view the narrowed graphene strip 205.

Figure 3:
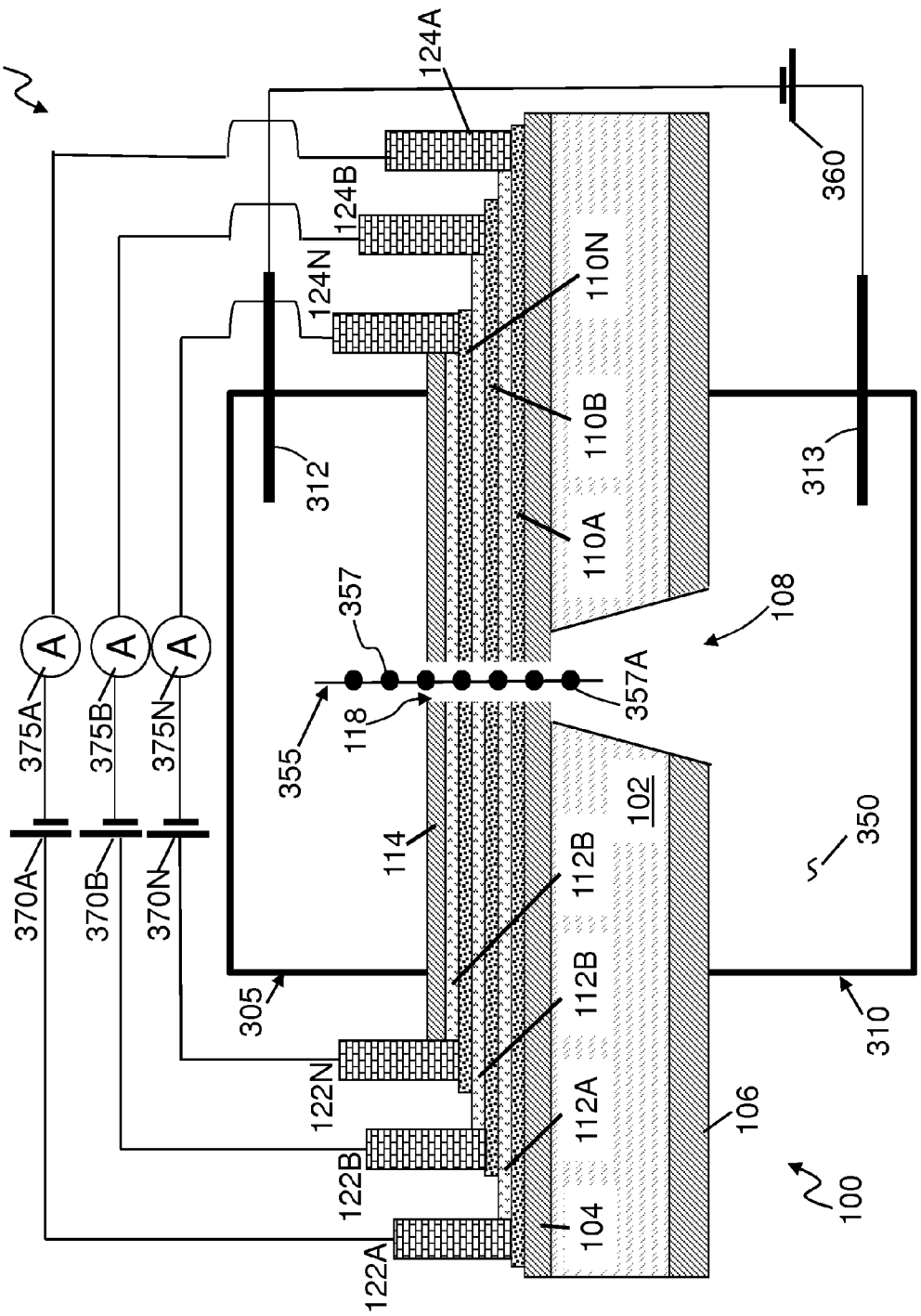
FIG. 3 schematically illustrates a cross-sectional view of the nanodevice in a system for sequencing molecules according to an embodiment.

Now turning to FIG. 3, a schematic illustrates a cross-sectional view of the nanodevice 100 in a system 300 for sequencing (DNA and/or RNA) molecules according to an embodiment. The system 300 includes all the layers of nanodevice 100 discussed herein in FIGS. 1 and 2.

The system 300 includes a top reservoir 305 attached and sealed to the top of the nanodevice 100 and a bottom reservoir 310 attached and sealed to the bottom of the nanodevice 100. The top reservoir 305, bottom reservoir 310, and nanopore 118 are all filed with an electrolyte solution 350 (ionic or buffer solution) that conducts electrical current. The electrolyte solution 350 may be a salt solution such as NaCl.

Electrode 312 is in the top reservoir 305, and electrode 313 is in the bottom reservoir 310. Electrodes 312 and 313 may be silver/silver chloride or platinum, for example.

Note that the graphene layers 110A through 110N may generally be referred to as graphene layers 110, and dielectric layers 112A through 112N may generally be referred to as dielectric layers 112. Also, metal electrodes 122A through 122N may generally be referred to as metal electrodes 122, and metal electrodes 124A through 124N may generally be referred metal electrodes 124.

First metal electrodes 122A and 124A act as a first pair of electrodes electrically connected to the graphene layer 110A. Second metal electrodes 122B and 124B act as a second pair of electrodes electrically connected to the graphene layer 110B. Similarly, last metal electrodes 122N and 124N act as the last pair of electrodes electrically connected to the graphene layer 110N.

A molecule 355, such as a DNA molecule for example, is in the top reservoir 305. Each base/nucleotide 357 of the molecule 355 is depicted as a solid oval connected to one another by a backbone (connecting line). The DNA molecule 355 may be a negatively charged molecule. The DNA molecule 355 is moved to (i.e., captured at the entrance (the top of nanopore 118) and through the nanopore 118 by applying a voltage from a voltage source 360 across electrodes 312 and 313. An electric field generated by the voltage of the voltage source 360 controllably drives the DNA molecule 355 through the nanopore 118 at a desired rate, e.g., by pulsating (i.e., repeatedly turning on and off) the voltage source 360. The voltage generates an electric field across the nanodevice 100 (via electrodes 312 and 313) to move the DNA molecule 355 as desired.

Once the DNA molecule 355 is in the nanopore 118, the respective voltages of voltage sources 370A, 370B, through 370N are turned on to individually generate electrical current that is respectively measured by corresponding ammeters 375A, 375B, through 375N.

For example, assume that a particular base 357A is in the nanopore 118 between the left and right side of the last graphene layer 110N. The voltage source 370N is applied via the (last) pair of metal electrodes 122N and 124N to generate electrical current. The electrical current flows from the last voltage source 370N, into last metal electrode 122N, into the left side of the last graphene layer 110N, into the nanopore 118 to interact with the particular base 357A, out through the right side of the last graphene layer 110N, and out through the last metal electrode 124N to be measured by the last ammeter 375N. This electrical current (signature) may be stored by a computer 500 for comparison (and eventual identification) against subsequent electrical current measurements of the same particular base 357A by the remaining graphene layers.

Now, the particular base 357A is moved to the next graphene layer which is graphene layer 110B (in this example), so that a second electrical current measurement may be performed via ammeter 375B. In this case, the voltage of the voltage source 370B is applied via the pair of metal electrodes 122B and 124B to generate electrical current. The electrical current flows from the voltage source 370B, into metal electrode 122B, into the left side of the last graphene layer 110B, into the nanopore 118 to interact with the particular base 357A, out through the right side of the graphene layer 110B, and out through the metal electrode 124B to be measured by the ammeter 375B. This electrical current (signature) may also be stored by the computer 500 for comparison (and eventual identification) against past and future electrical current measurements of the same particular base 357A.

By analogy, the same process occurs when the particular base 357A is moved between the left and right sides of the graphene layer 110A in the nanopore 118. The voltage of the voltage source 370A is applied to measure the electrical current when the particular base 357A is present in the nanopore 118 between the left and right sides of the graphene layer 110A. The electrical current is measured by the ammeter 375A and is again stored in the computer 500. Each of the electrical currents measured for the particular base 357A are compared (e.g., by the computer 500 and/or an operator) against known electrical currents (signatures) that respectively identify bases (such as bases A, G, C, and T) such that the individual electrical currents (which should be the same or statistically the same) for the particular base 357A are matched and identified accordingly.

Figure 5:
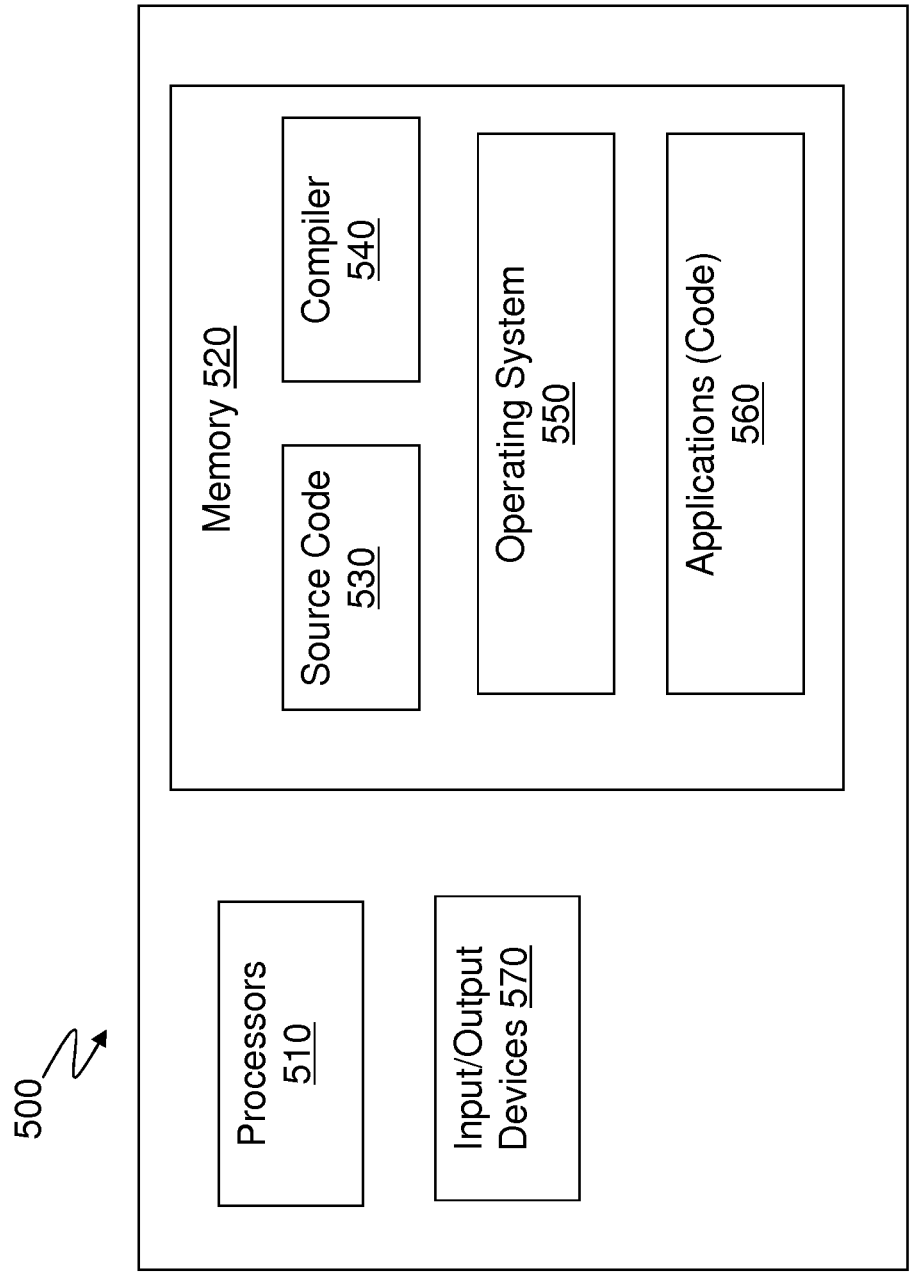
FIG. 5 is a block diagram that illustrates an example of a computer (computer test setup) having capabilities, which may be included in and/or combined with embodiments.

Note that the voltages sources 370, ammeters 375, and voltage source 360, along with individual electric current reading, can be implemented and controlled by a computer system 500 (test setup equipment) discussed in FIG. 5.

Although only three graphene layers 110 (which act as sensors) are connected to respective voltage sources 370 and ammeters 375 by wire and metal electrodes, there may be more than three graphene layers 110 (along with respective equipment and additional layers). For example, there may be 4, 5, 6, 7 . . . 10 or more graphene layers 110 (each respectively connected to its own metal electrodes 122 and 124, wire, voltage source 370, and ammeter 375) with each graphene layer having a corresponding dielectric layer 112 on top, as shown in FIGS. 1-3. Each of these, e.g., 10 graphene layers is utilized to repeatedly measure and generate individual electrical currents for the particular bases 357A, so that the particular base 357A can be matched.

Figure 4:
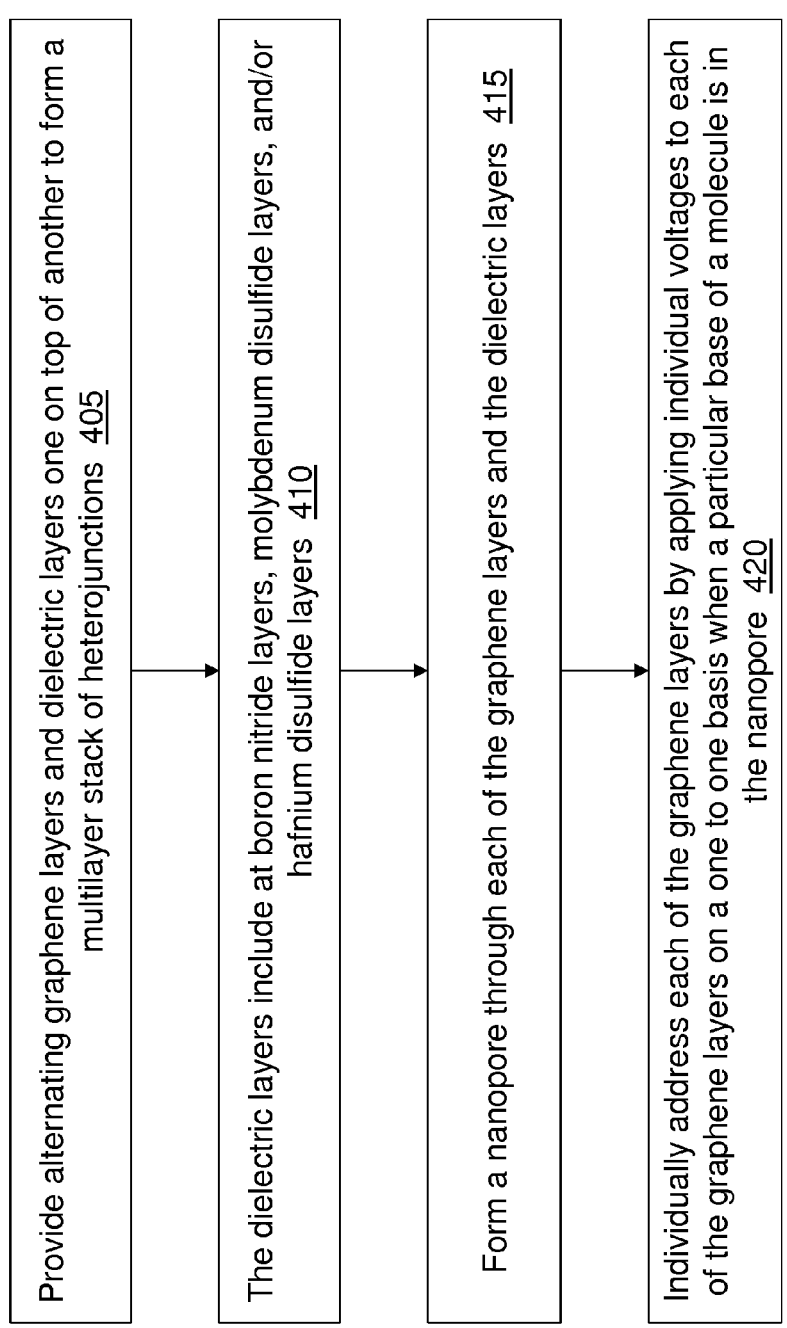
FIGS. 4A and 4B together illustrate a method of forming the nanodevice for sequencing according to an embodiment.

FIGS. 4A and 4B together are a method of forming the nanodevice 100 for sequencing according to an embodiment. Reference can be made to FIGS. 1-3 discussed herein (including FIG. 5 below).

Alternating graphene layers 110A-110N and dielectric layers 112A-112N are deposited/provided one on top of another to form a multilayer stack of heterojunctions at block 405. Each junction of the heterojunctions is the location in the nanopore 118 between, for example, the left side and right side of graphene layer 110 (graphene layer 110A) at which the electrical current for the base 357 is measured.

The dielectric layers 112 include at least one of boron nitride layers, molybdenum disulfide layers, and/or hafnium disulfide layers at block 410. In one case, each of the dielectric layers 112A-112N is boron nitride layer(s). In another case, each of the dielectric layers 112A-112N is molybdenum disulfide layer(s) ($MoS_2$). In one case, the dielectric layers 112A-112N may be alternating dielectric layers of boron nitride layer(s) and (then next) molybdenum disulfide layer(s).

A nanopore 118 is formed through each of the graphene layers 110 and the dielectric layers 112 (and optionally the insulating layer 114) at block 415.

Each of the graphene layers 110 is individually addressed by applying individual voltages (from respective voltage sources 370A-370N) to each of the respective graphene layers 110A-110N on a one to one basis when a particular base 357A of the molecule 355 is in the nanopore 118 at block 420. Each of the graphene layers 110A-110N is an electrode with a junction (for measuring electrical current change when the base 357 is in the junction) in the nanopore 118.

Individual electrical currents are respectively (repeatedly) measured for each of the graphene layers 110A-110N as the particular base 357A moves from a first graphene layer 110A through a last graphene layer 110N in the nanopore 118 (each base 357 is repeatedly measured (e.g., 3, 4, 5, 7, 9 times) at the various junctions in the nanopore 118) at block 425.

An identification of the particular base 357A is determined (by computer 500) according to the individual electrical currents repeatedly read/measured for the particular base 357A moving to the first graphene layer 110A (and measured) through the last graphene layer 110N (and measured) in the nanopore 118 (such that the individual electrical current for the particular base is measured at each junction) at block 430.

Determining the identification of the particular base according to the individual electrical currents being repeatedly read for the particular base is based on measured values of the individual electrical currents being a same or nearly the same. These measured values are matched (e.g., by the computer 500) to known (predetermined) electrical current values for known bases so that the particular base 357A can be identified as, e.g., base A, G, C, or T. Note that when the value of one of the individual electrical currents measured for the particular base 357A is off (e.g., deviates from the nearest/closest value of any of the individual electrical currents (which can be less than or greater than) by a predetermined amount or more (e.g., 0.5 picoamperes (pA), 0.8 pA, and/or 1 pA or more) from the other measured values of the electrical currents for the particular base 357A, the electrical current value that is off the predetermined amount (or more) is dropped and is not utilized as a value to match the known (predetermined) electrical current values for known bases. Instead, the remaining individual electrical current values (of the particular base 357A) are utilized by the computer 500 to match one of the known (predetermined) electrical current values for base A, G, C, or T.

The individual electrical currents each correspond to the (same) particular base 357A at different locations (i.e., different junctions between the left side and right side of respective graphene layers 110) in the nanopore 118. The individual electrical currents correspond to measuring via the graphene layers as the electrodes on a one to one basis, such that no graphene layer 110 measures the particular base 357A more than once (because the base moves on through the nanopore 118 to be measured by the next graphene layer 110). The number of the individual electrical currents measured for the particular base 357A at the different locations (each junction) in the nanopore 118 equals the number of the graphene layers 110A-110N.

The dielectric layers 112 may include layers of a combination of the boron nitride layers, the molybdenum disulfide layers, (and/) or hafnium disulfide layers in an alternating manner. The boron nitride layers each have one or few mono-layers of boron nitride. Each mono-layer of boron nitride has a thickness of 0.3 to 0.5 nanometers. The molybdenum disulfide layers each have one or few mono-layers of molybdenum disulfide. Each mono-layer of molybdenum disulfide has a thickness of 0.6 nanometers to 0.8 nanometers. The individual dielectric layers 112 are each atomically thin insulators. These materials (boron nitride, molybdenum disulfide, and hafnium disulfide) have a layered structure similar to graphite. Within each layer, atoms are bound by strong covalent bonds, whereas the layers are held together by weak van der Waals forces. Therefore atomically thin layer(s) (i.e., a mono-layers) can be obtained easily by exfoliation or chemical synthesis. The resulting atomically thin layers are continuous and mechanically strong. Boron nitride is an insulator; $MoS_2$ and HfS2 are wide band gap semiconductors.

FIG. 5 illustrates an example of a computer 500 (e.g., as part of the computer test setup for testing and analysis) which may implement, control, and/or regulate the respective voltages of the voltage sources, respective measurements of the ammeters, and display screens for displaying various electrical current amplitude (including ionic current) as discussed herein. The computer 500 also stores the respective electrical current amplitudes of each base tested and measured to be compared against the baselines current amplitudes of various known bases (predetermined in advance), which is utilized to identify the bases of the tested/target molecule.

Various methods, procedures, modules, flow diagrams, tools, applications, circuits, elements, and techniques discussed herein may also incorporate and/or utilize the capabilities of the computer 500. Moreover, capabilities of the computer 500 may be utilized to implement features of exemplary embodiments discussed herein. One or more of the capabilities of the computer 500 may be utilized to implement, to connect to, and/or to support any element discussed herein (as understood by one skilled in the art) in FIGS. 1-4. For example, the computer 500 which may be any type of computing device and/or test equipment (including ammeters, voltage sources, current meters, connectors, etc.). Input/output device 570 (having proper software and hardware) of computer 500 may include and/or be coupled to the nanodevices and structures discussed herein via cables, plugs, wires, electrodes, patch clamps, electrode pads, etc. Also, the communication interface of the input/output devices 570 comprises hardware and software for communicating with, operatively connecting to, reading, and/or controlling voltage sources, ammeters, and current traces (e.g., magnitude and time duration of current), etc., as discussed and understood herein. The user interfaces of the input/output device 570 may include, e.g., a track ball, mouse, pointing device, keyboard, touch screen, etc., for interacting with the computer 500, such as inputting information, making selections, independently controlling different voltages sources, and/or displaying, viewing and recording current traces for each base, molecule, biomolecules, etc.

Generally, in terms of hardware architecture, the computer 500 may include one or more processors 510, computer readable storage memory 520, and one or more input and/or output (I/O) devices 570 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 510 is a hardware device for executing software that can be stored in the memory 520. The processor 510 can be virtually any custom made or commercially available processor, a central processing unit (CPU), a data signal processor (DSP), or an auxiliary processor among several processors associated with the computer 500, and the processor 510 may be a semiconductor based microprocessor (in the form of a microchip) or a macroprocessor.

The computer readable memory 520 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 520 may incorporate electronic, magnetic, optical, and/or other types of storage media. Note that the memory 520 can have a distributed architecture, where various components are situated remote from one another, but can be accessed by the processor 510.

The software in the computer readable memory 520 may include one or more separate programs, each of which comprises an ordered listing of executable instructions for implementing logical functions. The software in the memory 520 includes a suitable operating system (O/S) 550, compiler 540, source code 530, and one or more applications 560 of the exemplary embodiments. As illustrated, the application 560 comprises numerous functional components for implementing the features, processes, methods, functions, and operations of the exemplary embodiments.

The operating system 550 may control the execution of other computer programs, and provides scheduling, input-output control, file and data management, memory management, and communication control and related services.

The application 560 may be a source program, executable program (object code), script, or any other entity comprising a set of instructions to be performed. When a source program, then the program is usually translated via a compiler (such as the compiler 540), assembler, interpreter, or the like, which may or may not be included within the memory 520, so as to operate properly in connection with the O/S 550. Furthermore, the application 560 can be written as (a) an object oriented programming language, which has classes of data and methods, or (b) a procedure programming language, which has routines, subroutines, and/or functions.

The I/O devices 570 may include input devices (or peripherals) such as, for example but not limited to, a mouse, keyboard, scanner, microphone, camera, etc. Furthermore, the I/O devices 570 may also include output devices (or peripherals), for example but not limited to, a printer, display, etc. Finally, the I/O devices 570 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 570 also include components for communicating over various networks, such as the Internet or an intranet. The I/O devices 570 may be connected to and/or communicate with the processor 510 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 560 is implemented in hardware, the application 560 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. An apparatus for sequencing, the apparatus comprising:
a nanodevice including:
alternating graphene layers and dielectric layers one on top of another to form a multilayer stack of heterojunctions, wherein the dielectric layers include at least one of boron nitride layers, molybdenum disulfide layers, and hafnium disulfide layers, and wherein the graphene layers include a first graphene layer, a second graphene layer, and a third graphene layer; and
a nanopore through each of the graphene layers and the dielectric layers; and
pairs of electrodes individually addressed to each of the graphene layers, the electrodes applying individual voltages to each of the graphene layers on a one to one basis when a particular base of a molecule is in the nanopore, wherein the first graphene layer is connected to a first pair of electrodes for a first measurement, the second graphene layer is connected to a second pair of electrodes for a second measurement, and the third graphene layer is connected to a third pair of electrodes for a third measurement.

2. The apparatus of claim 1, further comprising:
a test setup, wherein the test setup is configured to respectively measure individual electrical currents for each of the graphene layers as the particular base moves from a first graphene layer through a last graphene layer in the nanopore; and
wherein the test setup is configured to determine an identification of the particular base according to the individual electrical currents repeatedly measured for the particular base moving from the first graphene layer through the last graphene layer in the nanopore.

3. The apparatus of claim 2, wherein the test setup is configured such that determining the identification of the particular base according to the individual electrical currents repeatedly measured for the particular base is based on measured values of the individual electrical currents being a same or nearly the same.

4. The apparatus of claim 2, wherein the test setup is configured such that the individual electrical currents each correspond to the particular base at different locations in the nanopore.

5. The apparatus of claim 2, wherein the test setup is configured such that the individual electrical currents correspond to measuring via the graphene layers as the electrodes on a one to one basis, such that no graphene layer measures the particular base more than once.

6. The apparatus of claim 2, wherein the test setup is configured such that a number of the individual electrical currents measured for the particular base at a location of each graphene layer in the nanopore equals a number of the graphene layers.

7. The apparatus of claim 1, wherein the boron nitride layers each have one or few mono-layers of boron nitride;
wherein each mono-layer of the boron nitride has a thickness of 0.3 nanometers to 0.5 nanometers;
wherein the molybdenum disulfide layers each have one or few mono-layers of molybdenum disulfide; and
wherein each mono-layer of the molybdenum disulfide has a thickness of 0.6 nanometers to 0.8 nanometers.

* * * * *